United States Patent
Wang et al.

(10) Patent No.: US 7,676,255 B2
(45) Date of Patent: Mar. 9, 2010

(54) SYSTEM AND METHOD FOR SUPPORTING A PATIENT DURING MEDICAL IMAGING

(75) Inventors: Sharon Xiaorong Wang, Hoffman Estates, IL (US); Douglas Jay Wagenaar, South Barrington, IL (US); Ansgar Graw, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 611 days.

(21) Appl. No.: 11/384,929

(22) Filed: Mar. 20, 2006

(65) Prior Publication Data

US 2007/0238949 A1    Oct. 11, 2007

(51) Int. Cl.
   *A61B 5/05*    (2006.01)
(52) U.S. Cl. .................. 600/415; 5/600; 5/601; 5/620; 600/407; 600/437; 600/410; 600/425; 600/473
(58) Field of Classification Search .......... 600/415; 5/600, 601, 620
   See application file for complete search history.

(56) References Cited

U.S. PATENT DOCUMENTS

| | | | |
|---|---|---|---|
| 3,766,384 A * | 10/1973 | Anderson | 378/209 |
| 4,474,364 A * | 10/1984 | Brendgord | 5/619 |
| 4,688,780 A | 8/1987 | Hanz | |
| 6,684,095 B1 * | 1/2004 | Bonutti | 600/415 |
| 7,379,769 B2 * | 5/2008 | Piron et al. | 600/415 |
| 7,418,750 B2 * | 9/2008 | Haughton et al. | 5/601 |
| 2004/0176676 A1 | 9/2004 | Graw | |
| 2004/0255383 A1 * | 12/2004 | Longton | 5/601 |

* cited by examiner

*Primary Examiner*—Long V Le
*Assistant Examiner*—Nigel Fontenot
(74) *Attorney, Agent, or Firm*—Peter L. Kendall

(57) ABSTRACT

A medical imaging system having a patient support apparatus is provided. The medical imaging system includes a framework portion and a kit of rigid modular patient support panels, constructed of material having a radiation attenuation coefficient less than that of metals. The panels in sub-combination are removably mounted to and supported by the framework portion. The panels are selectively assembled to define varying surface profiles, including selective gaps there between, that are capable of conforming a patient in contact with the surface profile in a range of supported body positions from supine to seated.

25 Claims, 7 Drawing Sheets

SYSTEM AND METHOD FOR SUPPORTING A PATIENT DURING MEDICAL IMAGING

BACKGROUND

This disclosure relates generally to a diagnostic imaging system, and more particularly to a diagnostic imaging system having a patient support apparatus for physically supporting the patient during imaging by an imaging device of the diagnostic imaging system. In its most immediate sense, the disclosure relates to a diagnostic imaging system having a nuclear medicine imaging device and a patient support apparatus for supporting the patient during imaging by the nuclear medicine imaging device.

Nuclear medicine imaging assesses the radionuclide distribution within a patient after an in vivo administration of radiopharmaceuticals. The imaging systems that assess the radionuclide distribution include radiation detectors and associated electronics. The assessment includes detecting a nuclear decay event, where each detected nuclear decay event is referred to as a count.

In one prior art nuclear medicine imaging system using an emission camera the patient is supported on a table providing a single fixed planar surface for the patient to lie on. The emission camera is provided within the inner walls of a chamber formed within a tunnel shaped structure. The table is mobile for being received within the chamber. By rotating the emission camera relative to the patient, the emission camera images the patient at a variety of angles for acquiring image data in 3-dimensions. The patient is expected to remain still during the duration of the imaging study. Disadvantages associated with positioning the patient on the table and within the chamber include discomfort related to claustrophobia, discomfort remaining stationary and supine on the planar table, and isolation of the patient from medical practitioners.

Another prior art nuclear medicine imaging system includes an imaging device supported on an arm supported by a structure, such as a gantry or a wall, and a patient support apparatus configured as a table or pallet, where the table provides a single fixed planar surface for the patient to lie on. The gantry and/or arm is adjustable for moving the imaging device so that the patient supported on the table is in the field of view of the imaging device. Disadvantages associated with positioning the patient on the table during imaging using the supported imaging device include patient discomfort and difficulty in remaining stationary without shifting position for the duration of the imaging study.

In a prior art nuclear medicine imaging system described by U.S. Patent Application No. 2004/0176676, a chair-type patient support apparatus is provided. The described imaging device may be provided in combination with the patient support apparatus or as a separate unit. The chair may be positioned in an upright position or a reclining position. The chair may be provided with a back, seat and leg support, where the back and seat may be rotated relative to one another about a hinge, and the seat and leg support may be rotated relative to one another about a hinge.

Disadvantages associated with the chair-type patient support apparatus described is that supportive material used for the back, seat and leg support sections of the chair for supporting the patient's weight contributes to undesirable attenuation of radiation emitted during the imaging study. The materials forming each of the back, seat and leg must be sufficiently strong to provide the necessary support, and accordingly must have the necessary thickness and denseness to provide the support. The material of the portion of the chair that contacts the patient near a region of interest (ROI) being imaged contributes the most significant attenuation. For example, during a cardiac imaging study in which a patient is seated in a reclining position with the back of the patient supported by the back portion of the chair, the material of the chair contacting the back of the patient that is behind the heart of the patient contributes the most significant attenuation.

Furthermore, there are limitations to the positions that the chair may assume. Additionally, the chair size is fixed, and the shape of each of the back, seat and leg support elements is fixed. The chair is not configurable for patients of different sizes or shapes, or for accommodating different types of imaging studies corresponding to different ROIs (e.g., cardiac, prostrate, etc.). A close juxtaposition of the camera relative to the ROI contributes to good image quality. The camera may include a single-head or dual-head detector which needs to be positioned as closely as possible to the ROI. The structure of the chair is likely to interfere with placement of the camera in close juxtaposition to a ROI of a patient when the chair is used for a variety of different types of imaging studies which correspond to different ROIs and the use of single or double-head detectors.

To overcome the drawbacks in the prior art, it is an aspect of the present disclosure to provide a nuclear medicine imaging system having a patient support apparatus that is configurable for minimizing attenuation during an imaging study, where the patient support apparatus is used for a variety of different types of imaging studies which correspond to different ROIs.

It is a further aspect of the present disclosure to provide a nuclear medicine imaging system having a patient support apparatus that is configurable for accommodating patients of different sizes and shapes.

It is a further aspect of the present disclosure to provide a nuclear medicine imaging system having a patient support apparatus that is configurable for allowing of a camera of the imaging system to be in close juxtaposition to a ROI of a patient, where the patient support apparatus is used for a variety of different types of imaging studies which correspond to different ROIs.

SUMMARY

In accordance with an aspect of the present disclosure there is provided a medical imaging system having a patient support apparatus. The medical imaging system includes a framework portion; a first set of at least one panel removably mounted to and supported by the framework portion and for supporting a patient during a first imaging study by the medical imaging system; and a second set of at least one panel removably mounted to and supported by the framework portion after removal of the first set of at least one panel from the framework portion. The second set of at least one panel replaces the first set of at least one panel and supports the patient during a second imaging study by the medical imaging system.

In accordance with another aspect of the present disclosure, there is provided a patient support apparatus for supporting a patient during a medical procedure including a framework portion; a first set of at least one panel removably mounted to and supported by the framework portion and for supporting a first patient during a first medical procedure; and a second set of at least one panel removably mounted to and supported by the framework portion after removal of the first set of at least one panel from the framework portion. The second set of at least one panel replaces the first set of at least one panel and supports a second patient during a second medical procedure.

Pursuant to another aspect of the present disclosure, there is provided a medical imaging system having a patient support apparatus comprising: a framework portion having a base; a medical imaging device mounted to the base of the framework portion; a first set of at least one panel removably mounted to and supported by the framework portion and for supporting a patient during a first imaging study by the medical imaging system; and a second set of at least one panel removably mounted to and supported by the framework portion after removal of the first set of at least one panel from the framework portion. The second set of at least one panel replaces the first set of at least one panel and supports the patient during a second imaging study by the medical imaging system.

BRIEF DESCRIPTION OF THE DRAWINGS

Various embodiments of the present disclosure will be described herein below with reference to the figures wherein.

DETAILED DESCRIPTION OF THE PREFERRED EMBODIMENTS

Figure 1:
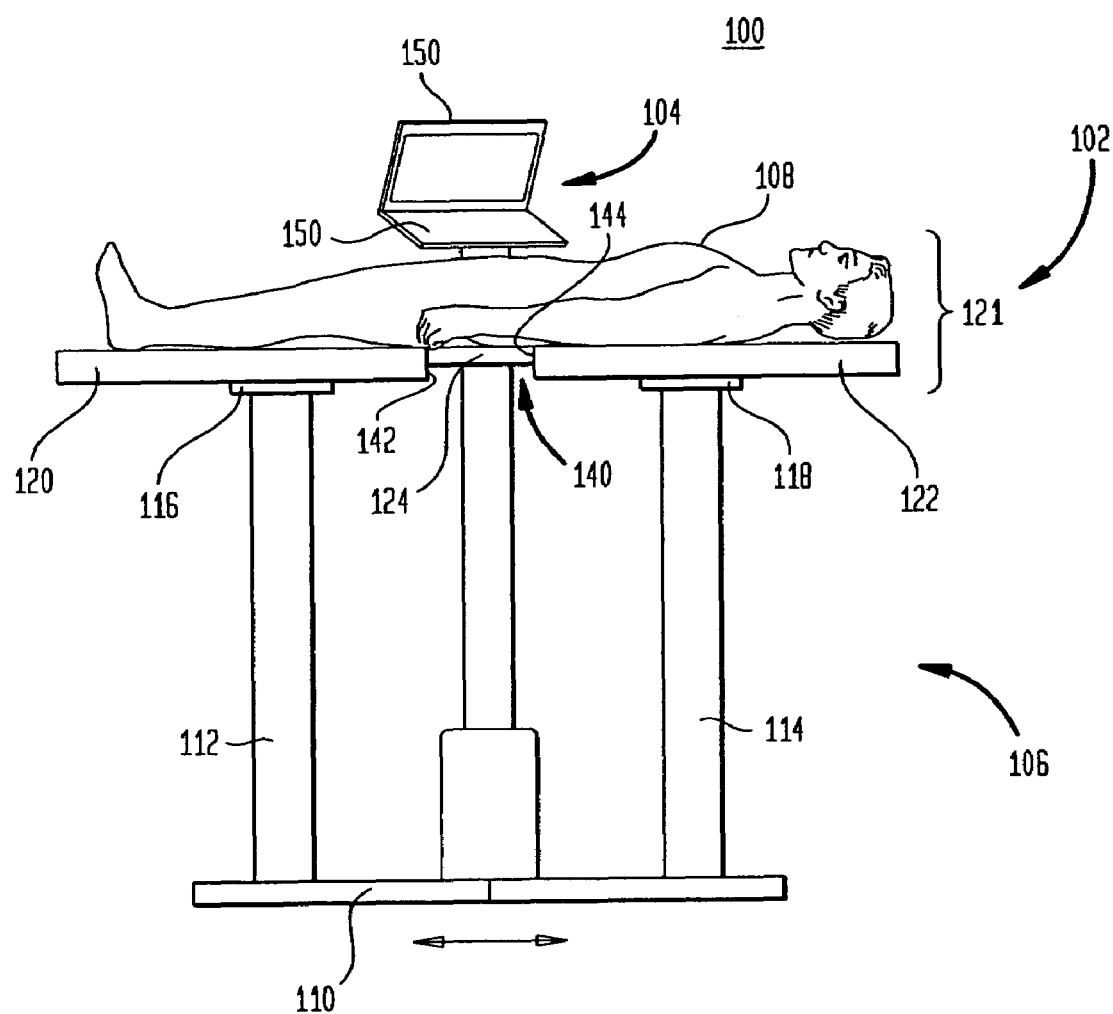
FIG. 1 is a side view of a nuclear medicine imaging system having a patient support apparatus in accordance with the present disclosure.
Figure 2:
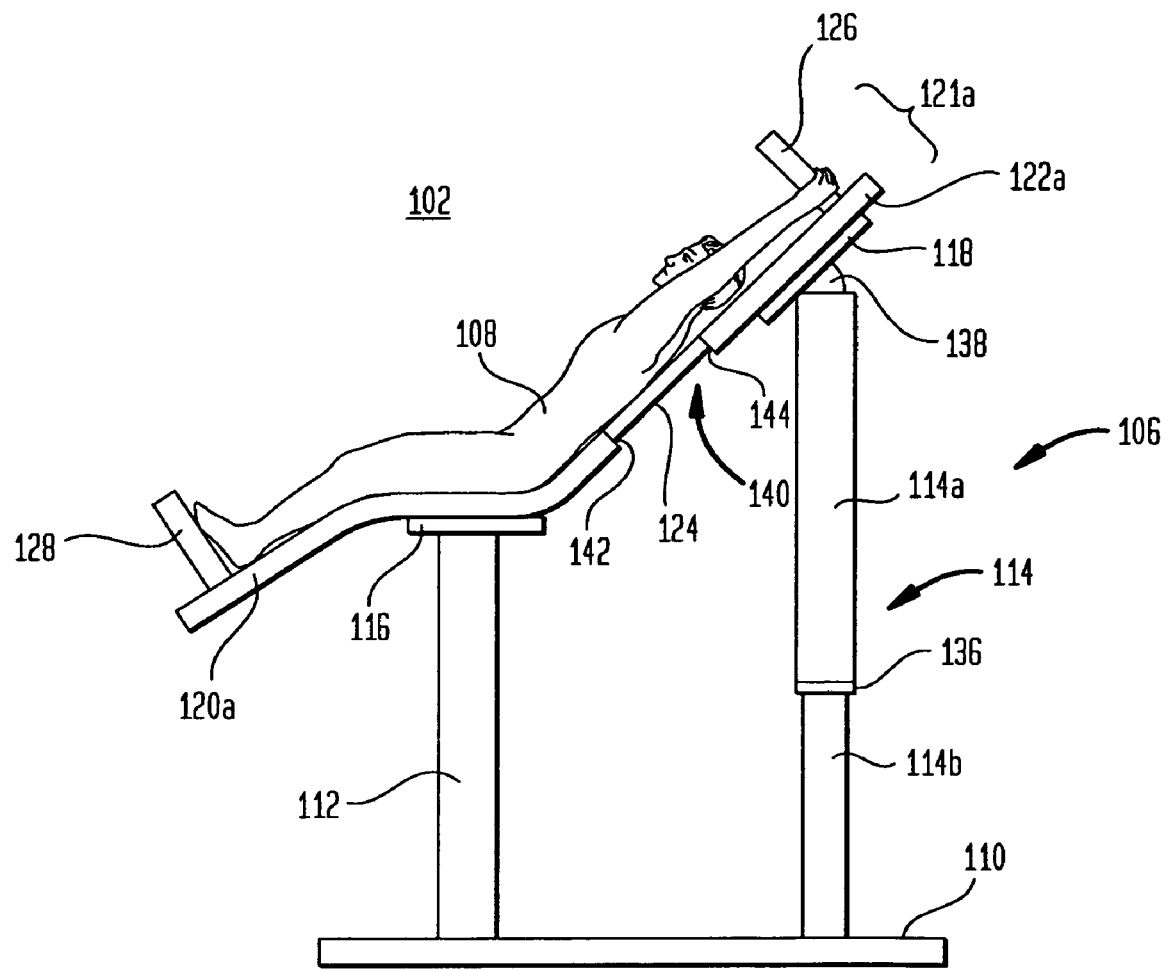
FIGS. 2-3 are side views of different configurations of the patient support apparatus shown in FIG. 1.
Figure 3:
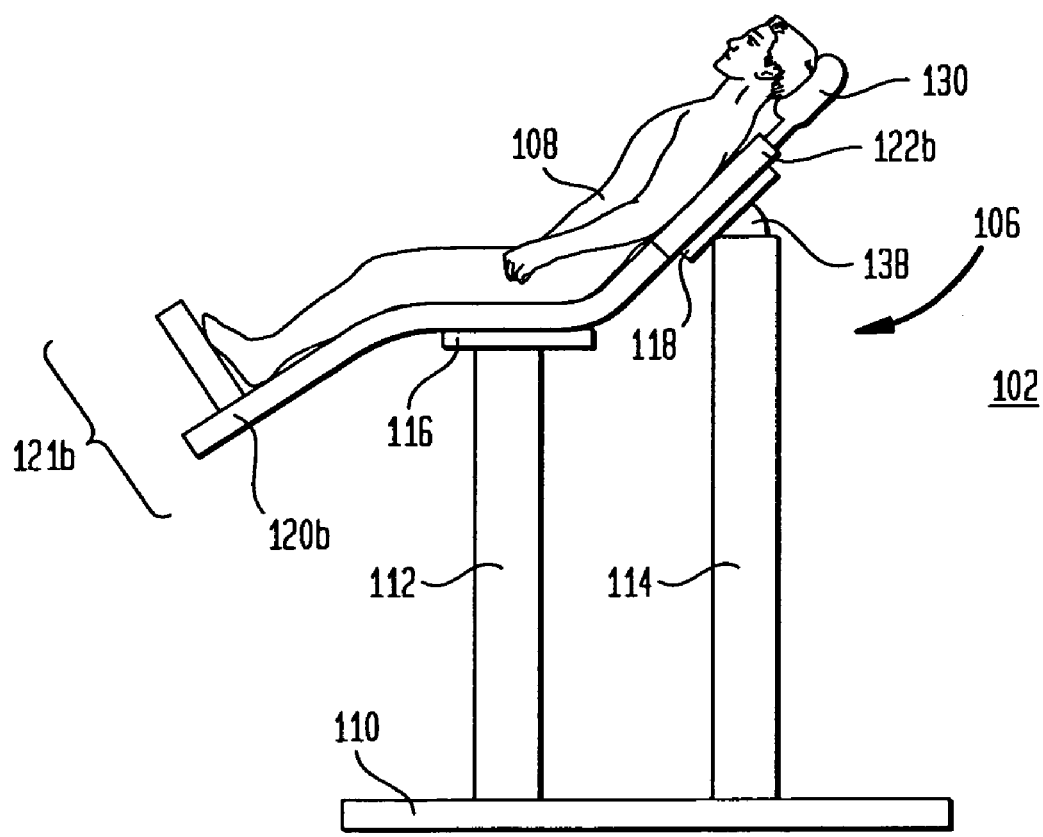

For a general understanding of the features of the present disclosure, reference is made to the drawings. In the drawings, like reference numerals have been used throughout to identify identical elements. With reference to FIGS. 1-3, an exemplary medical imaging system in accordance with the present disclosure is illustrated and is designated generally as imaging system 100. Imaging system 100 includes a patient support apparatus 102 (shown in accordance with a first configuration in FIG. 1) and a medical imaging device 104 supported by a supporting structure 104. A patient 108 is supported by the patient support apparatus 102 during an imaging study of a region of interest (ROI) of the patient 108. In the disclosure, the medical imaging system 100 is described as an exemplary nuclear medical imaging system, and the medical imaging device 104 is described as an exemplary nuclear medical imaging device, however the disclosure is not limited thereto.

The patient support apparatus 102 includes a framework portion 109, which in the example provided includes a base 110, at least first and second posts 112 and 114, respectively, and at least first and second plates 116 and 118, respectively. The patient support apparatus 102 further includes a first set 121 of at least one supporting panel, shown exemplarily as including first and second supporting panels 120 and 122, and optionally panel insert 124. FIGS. 1, 2 and 3 show the patient support assembly 102 in accordance with first, second and third configurations, respectively. As shown in FIG. 1, the panels 120, 122 and optional panel insert 124 form a bed for supporting the patient 108 in a supine position. As shown in FIG. 2, the panels 120a, 122b and optional panel insert 124 form a reclining chair, and the patient support apparatus 102 further includes a hand grasp attachment 126 and a foot rest attachment 128. As shown in FIG. 3, the patient support apparatus 102 further includes a headrest attachment 130.

The patient support apparatus 102 is reconfigurable by adjusting the framework portion 106 and/or interchanging the first set of panels 121 with a second set of at least one panel 121a shown in FIG. 2, including panels 120a and 122a, and a third set of at least one panel 121b shown in FIG. 3, including panels 120b and 122b. A gap, described further below, may be provided between the panels 120 and 122. The gap may be adjusted by at least one of adjusting the framework portion 106, interchanging the first and second sets of panels, and adjusting the mounting of at least one of the first and second panels to the framework 106.

Figure 4:
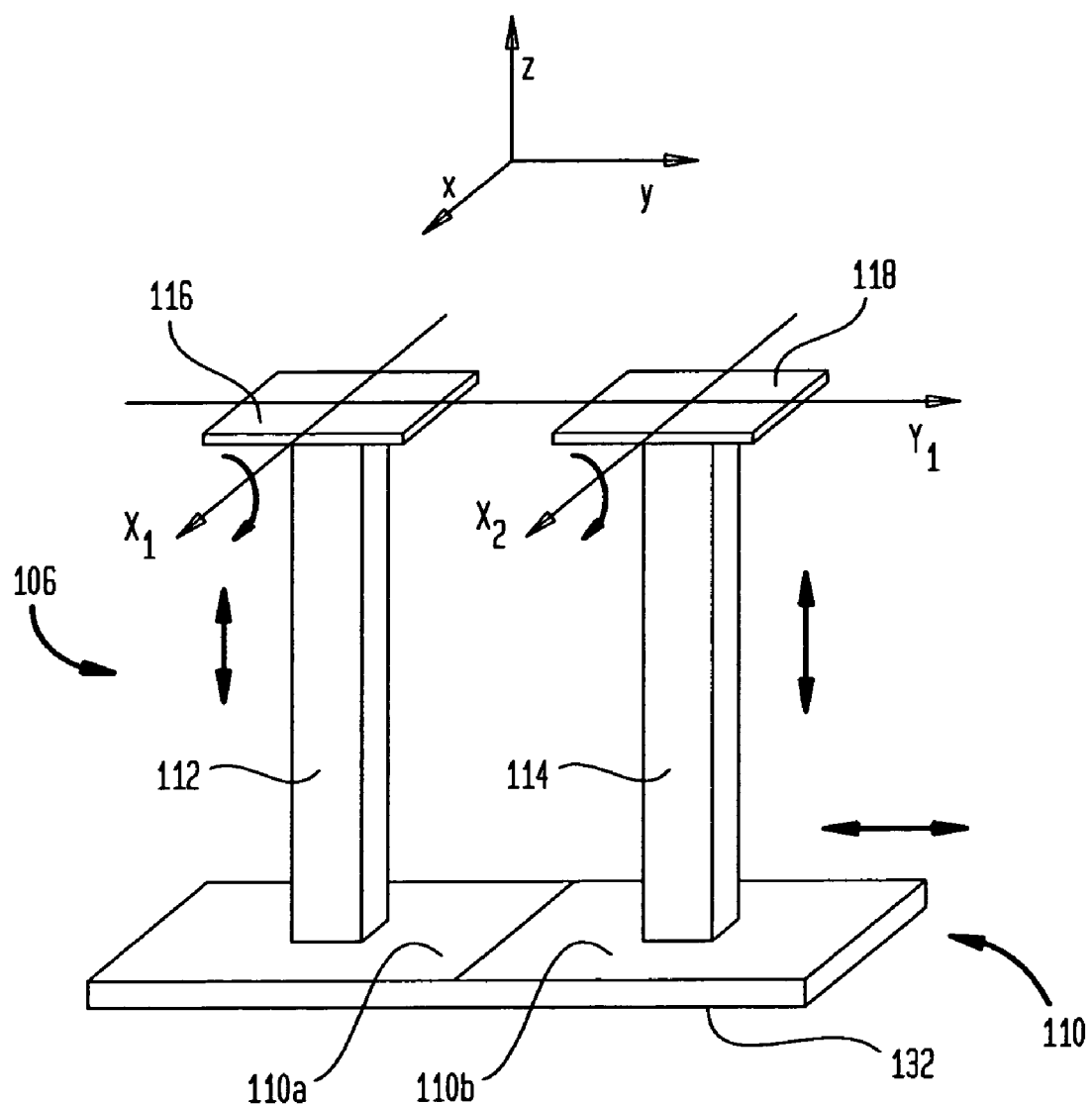
FIG. 4 is a perspective view of a framework portion of the patient support apparatus shown in FIG. 1.

With reference to FIG. 4, an exemplary embodiment of the framework portion 106 of the patient support apparatus is shown in greater detail. The base 110 rests on a floor, and is immobilized for preventing movement relative to the floor, such as by anchoring the base to the floor, or providing the base with a mechanism for preventing movement relative to the floor. The base 110 may be provided with wheels (not shown) mounted to its bottom surface 132 for providing the patient support apparatus 102 with mobility. The wheels may be retracted, removed or immobilized with brakes for immobilizing the base 110 relative to the floor. The base 110 may be formed of a single plate, or include first and second plates 110a and 110b mounted on a frame (not shown) that are moveable along the frame in the Y direction relative to one another for increasing the length of the base 110. The base 110 and/or posts 112 and 114 may be provided with a mechanism for allowing movement of posts 112 and 114 relative to one another, such as by sliding or rolling the posts 112, 114 along a channel provided in the base 110. In another embodiment of the disclosure, the posts 112 and 114 may be mounted at a variety of locations along base 110. Alternatively, posts 112 and 114 may be mounted to the floor.

First post 112 is mounted to the base 110, which may include being mounted to plate 110a of the base 110 when provided. Second post 114 is mounted to the base 110, which may include being mounted to plate 110b of the base 110 when provided. Exemplary mountings for the posts 112 and 114 to the base include bolting, soldering, snap fitting, screwing, clamping, fastening, dovetailing, etc.

The posts 112 and 114 may be removably attached to the base 110, such as for the purpose of disassembling the patient support apparatus 102. At least one of posts 112 and 114 are provided with a height adjusting mechanism for independently adjusting the height of at least one of post 112 and 114. For example, post 114 may be provided with telescopic portions that expand from a first height to at least a second height and a braking mechanism for securely maintaining the height selected, even when a force is applied to the posts 112 and 114, such as by the weight of a patient 108 being supported by patient support apparatus 102. Exemplary telescopic portions 114a and 114b are shown in FIG. 3, with braking mechanism 136 that locks the height adjusting mechanism and maintains the selected height, even while the patient is supported on the patient support apparatus 102. Other prior art mechanisms for providing adjustability of height to posts 112 and 114 while withstanding the force of a supported patient 108 (e.g., a screw and motor combination, and a hydraulic mechanism) are included in the scope of the disclosure. Additionally, a control system may be provided for controlling a motor of the height adjusting mechanism for saving the setting of a satisfactory height position or facilitating height adjustment for achieving a desired height position, such as provided by user input or a host computer.

A rotatable mount mechanism 138 is provide for rotatably mounting plate 116 to post 112, and plate 118 to post 114 for allowing plates 116 and 118 to pivot relative to the posts 112 and 114, respectively, e.g., about axes $X_1$ and $X_2$, respectively, or to swivel relative to posts 112 and 114 about additional axes (e.g., axis $Y_1$). Such rotation (including pivoting and/or swiveling) may be limited for assuring safe and secure positioning of the patient on the patient support apparatus 102. The rotatable mount mechanism 138 may include a hydraulic system and/or motor (e.g., where the motor turns a shaft that turns a gear for causing the rotation of the plate 116 or 118) for facilitating rotation. Only one of the plates or both of the plates 116 and 118 may be rotatably mounted. Additionally, plates 116, 118 may be rotated independently of one another. The angle and direction of rotation relative to the reference plane is measurable and preferably selectable. A control system may be provided for controlling a motor of the rotatable mount mechanism 138 for saving the setting of a satisfactory angular position relative to the reference plane and/or facilitating rotation for achieving a desired angular position, such as provided by user input or a host computer.

The bed or chair formed by panels 120, 122 and optional panel insert 124 may be raised or lowered, e.g., for loading and unloading of the patient 108. The aforementioned raising or lowering may be achieved by simultaneously lengthening or shortening posts 112 and 114 at the same rate without changing the angle of incline of plates 116 and 118. The raising and lowering of the bed or chair may be performed while supporting patient 108.

The framework portion 106 provides support for countering the force of the patient's weight while the patient is supported by the patient support apparatus 102. The framework portion 106, e.g., the base 110, posts 112 and 114, and plates 116 and 118, are fabricated of at least one material, including a supportive material, such as metal, providing the necessary support. In order to minimize attenuation of radiation during imaging, the surface area of the plates 116 and 118 is minimized. Furthermore, in the embodiment shown, the surface area of the plates 116 and 118 is greater than the area of the cross section of the posts 112, 114 upon which the respective plates 116, 118 are mounted. Furthermore, the connecting structures for connecting the posts 112 and 114 to the base 110, and for connecting the plates 116 and 118 to the respective posts 112, 114, are also fabricated of at least one material, including a supportive material, such as metal, for providing the necessary support.

With respect to FIGS. 2-4, the patient support apparatus 102 is shown in different configurations for accommodating a variety of patient sizes, patient positions (e.g., sitting upright, sitting reclining, lying supine) and clinical needs. Panel 120, a body and sitting support, is removably mounted to plate 116. Panel 122, a head support and/or chair back, is removably mounted to plate 118. The surface area of panel 120 is several times larger than the surface area of plate 116, and the surface area of panel 122 is several times larger than the surface area of plate 118.

When panels 120 and 122 are mounted to their respective plates, they are securely mounted to ensure that the panels will not be unintentionally disengaged from their respective plates. It is desirable that disengagement and reengagement of panels 120 and 122 from their respective plates, and securing of the panels 120 and 122 to their respective plates, may be performed by one operator, such as in-between treating a first patient and a second patient for changing the configuration of the patient support apparatus 102 in accordance with the imaging study being performed for each patient, and the size and positioning of the respective patients.

A variety of panels 120, 122 may be provided, each panel 120, 122 having a different shape, curvature, size or configuration for accommodating patients of varying sizes (e.g., pediatric, adult and obese patients), patient positions, and a variety of clinical needs. The panels 120, 122 may vary in curvature along a longitudinal (parallel to the Y-axis) or a transverse axis (parallel to the X-axis). Variation in curvature along the longitudinal axis, for example, accommodate a variety of lying, sitting and postural positions and patient heights, while providing the patient with comfort. Variation of curvature along the transverse axis, for example, accommodates a variety of patient widths, while providing comfort and a sense of security to the patient. The curvature along the transverse axis may be particularly accentuated when rotation of plates 116 and 118 is provided about axis $Y_1$. Additionally, panels 120 and 122 may be provided with structures for securing one or more safety or comfort devices, such as cushions or straps. The safety straps are used for securing the patient 108 in order for the patient 108 to be securely supported on the patient support apparatus 102 and for the patient 108 to perceive that he is safe.

It is desirable to minimize an attenuation coefficient of the panels 120 and 122 for not interfering with radiation detection during the imaging study by the medical imaging device 104. Accordingly, it is desirable to minimize the thickness of the panels 120 and 122 for minimizing the attenuation coefficient, and use a material that has a minimal attenuation coefficient. Panels 120 and 122 are made of a rigid material, such as fiberglass or molded carbon fiber that is less dense than metal and has a significantly lower attenuation coefficient than metal. Exemplary materials that would not be appropriate for panels 120 and 122 due to their high attenuating properties include steel, copper, iron, gold, lead, nickel, platinum, silver, tantalum, tungsten, tin, zinc, or any alloy or composite that contains substantial quantities of any of these elements, alone or in combination (e.g., >10% by weight). The use of any of the aforementioned materials, alloys or composites is minimized or eliminated in the portions of the patient support apparatus 102 that may be positioned near the ROI of the patient 108.

The rigid material is sufficiently rigid to maintain its shape even while supporting a patient 108. The panels 120 and 122 should not deform under the weight of the patient 108 or if the patient 108 exerts additional force, such as if he shifts his weight or changes position while being supported by the patient support apparatus 102. Generally, the patient support apparatus 102 should not move, shift or deform under the weight of the patient 108 or in response to any force exerted by the patient 108 while supported by the patient support apparatus 102 in order that the patient 108 remain motionless during an imaging study.

Any of the panels described may be provided with adjustment mechanisms for changing the configuration of the panel itself. Once the adjustment is made, the panel must be locked in that position and configuration so that no motion of the patient will occur during an imaging study.

FIG. 3 shows panels 120*a* and 122*a* with the patient support apparatus 102 configured in one configuration, and FIG. 4 shows panels 120*b* and 122*b*, with the patient support apparatus 102 configured in another configuration. Panel 120*a* is shorter than panel 120*b*, and panel 122*a* is shorter than panel 122*b*, defining a gap 140 in-between at least a portion of the top end 142 of panel 120*a* and at least a portion of the bottom end 144 of panel 122*a*.

The size and location of gap 140 may be adjusted by selecting different panels 120 and 122, adjusting how the panels 120 and 122 are mounted to the respective plates 116 and 118, and/or adjusting the positions of the posts 112 and 114 relative to one another. The size and location of the gap 140 may be selected for accommodating the size of the patient and the clinical purpose. For example, gap 140 may be provided adjacent to the patient's chest for performance of a cardiac imaging study, adjacent the pelvic area for performance of a pelvic (e.g., uterine or prostrate) imaging study and adjacent the abdomen for performance of an abdominal imaging study, etc.).

Gap 140 provides advantages for image acquisition. One advantage includes providing complete or maximized transparency to detectors 150 of medical imaging device 104. Another advantage includes assuring that detectors 150 are not obstructed for being closely juxtaposed to the patient 108, and for achieving a full range of movement where applicable for mobile detectors 150 (e.g., for rotation of the detectors 150 about the ROI of the patient 108). The ability to configure the patient support apparatus 102 in a variety of configurations in which the gap 140 may be provided at a selected location maximizes the advantages provided by gap 140 for a variety of clinical usages. For example, the patient support apparatus is configured for positioning the gap 140 behind the patient's 108 heart during a cardiac imaging study, behind the patient's upper abdomen during a thorax imaging study, and behind the patient's pelvic region during a pelvic imaging study.

At least one releasable mechanical fastening structure is provided for mounting the panels 120 and 122 to plates 116 and 118, respectively, so that the panels 120 and 122 are replaceable with another set of panels. The at least one mechanical fastening structure may include a screw, clamp, mating or dovetailing structure, etc. In one embodiment of the disclosure, a first mating structure is provided on each of the bottom surfaces of panels 120 and 122 and a second mating structure is provided on the each of the top surfaces of plates 116 and 118. The first mating structure of panel 120 engages with the second mating structure of plate 116, and the first mating structure of panel 122 engages with the second mating structure of plate 118 for securing panel 120 to plate 116 and panel 122 to plate 118. The first and second mating structures may be disengaged for replacing the panel 120 or the panel 122 with another panel 120 or 122 for reconfiguring the patient support apparatus 102. The panels 120 and 122 or the plates 116 and 118 may be provided with more than one mating structure, each mating structure positioned in a different position, where using a selected mating structure for mounting one of the panels 120 or 122 determines the position of the panel 120 or 122 once mounted.

Each of the panels 120 or 122 may be provided with an associated code which identifies the panel 120 or 122 that can be sensed by a reader device provided with the nuclear medical imaging system 100. For example, the code associated with panel 120 may include an optical code or an RFID code stored in an RFID tag that identifies the panel 120. The reader device may sense and decode the code, and record the code by storing it on a storage device.

The configuration used for the patient support apparatus 102 for each imaging study may be recorded, such as by recording the heights of the posts 112 and 114, the positions of the posts 112 and 114 relative to the base 110 or one another, the angular position of the plates 116 and 118 with respect to the reference plane or another structure, identification (ID) codes for each of the panels 120 and 122 for identifying the panels used, and the position in which the panels 120 and 122 were mounted. The settings may be recorded manually or sensed and recorded automatically, e.g., in the storage device. Accordingly, the same settings may be used for subsequent imaging studies of the same patient, even when the time interval in-between the imaging studies is extended. By using the same settings for the subsequent imaging studies, unnecessary variables are eliminated. The settings may be set manually and/or automatically, such us via a control system.

Panel insert 124 is optionally disposed within gap 140. Panel insert 124 does not need to support the patient's weight, but is provided for providing the patient with a sense of comfort and/or a perceived sense of security. Panel insert 124 may be formed of a rigid or flexible material having a minimal thickness, which may be less than the thickness of panels 120 and 122. The material and thickness of the material used for panel insert 124 is selected in order that the transparency of panel insert 124 to radiation is maximized, and an attenuation coefficient of panel insert 124 be minimized. Accordingly panel insert 124 has a minimal affect on radiation that is radiated from the ROI for maximizing image quality of images acquired by medical imaging device 104.

Panels 120 and 122 may be provided with accessories, such as the foot rest 128 and the hand grasp 126, respectively. The foot rest 128 provides comfort and a sense of security to the patient 108. The hand grasp 126 as shown in FIG. 3 is grasped by the patient's 108 hands for positioning the patient 108 in a position that is ideal for a cardiac imaging study. One or more hand grasps 126 may be provided at other location(s) for positioning the patient 108, and/or allowing the patient 108 to feel secure and comfortable while grasping the hand grasps 126 during an imaging study other than of the cardiac type. The accessories may be molded with the corresponding panel, or may be provided as attachments to be mounted to the corresponding panel. A fastening mechanism is provided for mounting each of the foot rest 128 and the hand grasp 126 to the corresponding panel. The fastening mechanism is sufficiently strong to resist force exerted by the patient 108 by his feet or hands. The fastening mechanism may include a screw, bolt, clamp, etc.

The headrest 130 may be provided for supporting the patient's 108 head, such as during an imaging study of the head/brain. The headrest 130 is formed of a material having a low attenuation coefficient, such as fiberglass or carbon fiber, and has a minimal surface area for maximum transparency to radiation. For example, the attenuation coefficient of the headrest 130 may be lower than or the same as the attenuation coefficient of panel 122, and the thickness of the headrest 130 may be lesser than or the same as the attenuation coefficient of panel 122. The portion of the headrest 130 upon which the head is supported may be concave or cupped for cradling the patient's 108 head for inhibiting head movement and giving the patient 108 a sense of comfort, stability and security. The headrest 130 may be similar to a prior art headrest which is typically attached to a prior art patient support apparatus, however the headrest 130 is configured for being molded with panel 122 or mounted to panel 122 with a fastening mechanism, such as a screw, bolt, clamp, mating structures, etc.

Figure 5:
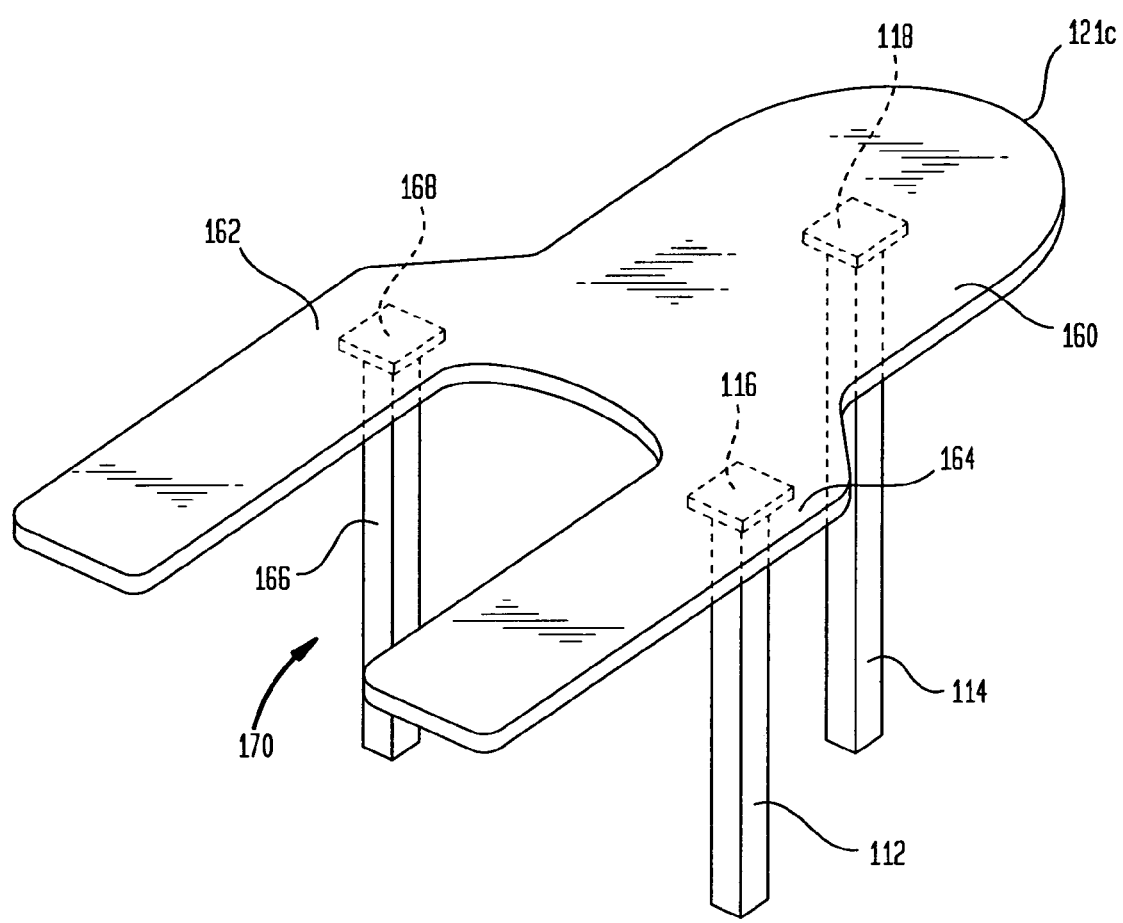
FIGS. 5-6 are perspective views of a portion of further different configurations of the patient support apparatus shown in FIG. 1.
Figure 6:
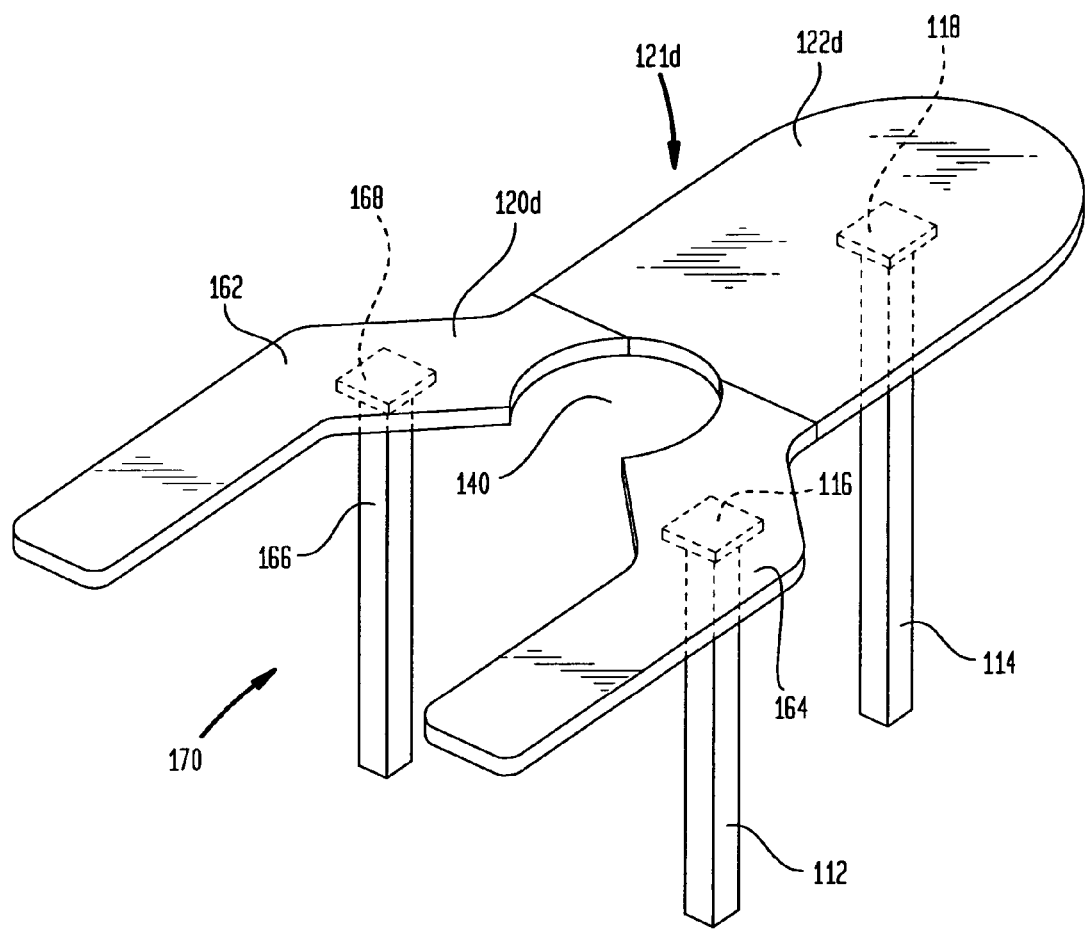

With respect to FIGS. 5 and 6, the patient support apparatus 102 is shown reconfigured for supporting a patient's legs while positioned in a straddle position. The exemplary configurations shown in FIGS. 5 and 6 may be used for performance of a pelvic imaging study. In FIG. 5, a fourth set of at least one panel 121c is shown including one panel 160 having portions 162 and 164 for supporting each of the patient's 108 respective legs. An additional post 166 and plate 168 is provided for supporting portion 162 and one of the patient's 108 legs. Post 112 has been relocated to a different location and together with plate 116 supports portion 164 and the other of the patient's 108 legs. Post 114 remains in its original position and together with plate 118 supports the remaining portion of panel 121*c*. Panel 121*c* is flat for allowing the patient to lie supine while supported thereupon. An open area 170 is described between portions 162 and 164. The open area provides space for a detector 150 to be placed in closely juxtaposition to the ROI being imaged.

In FIG. 6, a fifth set of at least one panel 121*d* is shown including panels 120*d* and 122*d*. The panel 122*d* is supported by post 114 and plate 118, with post 114 in its original location. Panel 122*d* having portions 162 and 164 is supported by post 112 and plate 116, and post 166 and plate 168. Post 112 is relocated to the different location. Posts 112, 114 and 166 form a tripod configuration. An open area 170 is described between portions 162 and 164 of panel 122*d*. Open area 170 merges with gap 140, which is described by panel 120*d*, with gap 140 lying below the patient's 108 pelvic area when the patient 108 is supported on the patient support apparatus 102. Open area 170 provides space for a detector 150 to be placed in close juxtaposition to the ROI being imaged. Panel insert 140 (not shown in FIG. 6) may be mounted on at least one of panel 120*d* and 121*d* for providing comfort and security to the patient 108. By providing gap 140, attenuation of radiation that is being detected at the ROI of the patient 108 is minimized by removing supportive material below the ROI.

With reference to FIGS. 5 and 6, with the patient 108 lying supine with straddled legs, one or more detectors 150 may be provided in close juxtaposition to the ROI from above patient 108, in close juxtaposition to the ROI from open area 170, or a combination thereof. In prior art nuclear medical imaging systems, the patient's pelvic area is scanned by detectors positioned near the patient's hips, which is relatively far from the ROI, such as when the ROI is the uterus or the prostrate. A further advantage provided by the configuration shown in FIGS. 5 and 6 is the absence of a post or plate from below the ROI for minimizing attenuation of radiation during the imaging. Additional posts may be provided for any configuration of the patient support apparatus 102. When a post is not being used it may be removed, relocated, or lowered so that it does not interfere with the patient support apparatus 102 or the imaging.

The medical imaging device 104 may be mounted to a gantry, arm or robot arm which may be mounted, for example, to a base, floor, wall or ceiling. The base of the medical imaging device 104 may be mobile for relocating the medical imaging device 104 to a new location. The gantry or base of the medical imaging device 104 may be positioned to only one side of the patient 108 and need not span to another side of the patient 108. In one embodiment of the disclosure, the base to which the medical imaging device 104 is mounted is further mounted to the base 110 of the patient support apparatus 102, using at least one fastening mechanism, such as a bolt, screw, clamp, mating structures, etc. For this embodiment, the base of the medical imaging device 104 is mounted to base 110 in a manner that will not interfere with adjustment of the base 110, such as for changing the distance between posts 112 and 114.

The medical imaging device 104 may be configured for a variety of types of nuclear medicine imaging, such as planar imaging or single-photon emission computerized tomography (SPECT) imaging. The medical imaging device 104 may include, for example, a single-head detector having one detector 150, or a multi-head detector having at least two detectors 150. The at least two detectors 150 may be configured so that they are fixedly positioned relative to one another at a predetermined angle. The detector(s) 150 may be stationary, be in motion (e.g., pivoting about an axis) during an imaging study, or include a plurality of scanning elements that are in motion, e.g., move up and down or move across the detector (150). The detector(s) 150 may be configured for imaging the head or brain of a patient. Head scan detector(s) may be disposed, for example, within a headpiece shaped as a ring or a helmet. Rotation of scanning elements or the detector(s) may take place within the headpiece, such as by rotating a collimator, for sensing from the perspective of a range of angles.

It is advantageous to position the detector(s) 150 of the medical imaging device 104 in close juxtaposition to the ROI of the patient 108 for acquiring images during nuclear medical imaging. In order to achieve the close juxtaposition to the ROI by the detector(s) 150 it may be desirable to position the detector(s) 150 at a predetermined angle with respect to the patient's 108 body. In a typical prior art patient support apparatus, structure of the patient support apparatus may interfere with the detector(s) achieving such a close juxtaposition and predetermined angle. When the detector(s) are moving, e.g., for pivoting about the ROI of the patient 108, the structure of a prior art patient support apparatus typically interferes with the range of motion of the detector(s).

Even if the prior art patient support apparatus is designed for a particular imaging study, such as a cardiac imaging study, such as by providing a fixed cut-away area of the patient support apparatus for accommodating the detector(s), the structure of the patient support apparatus is not configurable for accommodating the detector(s) in another type of an imaging study of a different ROI, or for another size patient 108. A fixed cut-away cannot be repositioned at a different location for acquiring images of a different ROI or imaging a patient 108 of a different size for minimizing or eliminating interference of the structure of the patient support apparatus with positioning and/or movement of the detector(s).

In the present disclosure, the position of the gap 140 is reconfigurable for accommodating the detector(s) 150 positioned at different locations for a variety of types of imaging studies and patient sizes. Patient support apparatus 102 can be reconfigured by strategically repositioning gap 140 from one location to another in accordance with the type of imaging study being performed or size of the patient 108 being treated in order that the structure of the patient support apparatus 102 not interfere with positioning of the detector(s) 150.

In accordance with the present disclosure, the detector(s) 150 may be positioned within the gap 140 and to the side or below the patient support apparatus 102 for imaging the patient 108 from another perspective other than from above the patient 108. Accordingly, the patient 108 may be imaged from a perspective associated with an angle ranging form 0°-360° about the patient 108.

The patient support apparatus 102 is a modular apparatus, in which a combination of modules may be selected from a variety of available modules for configuring the patient support apparatus 102. A particular clinic may purchase a set of modules that are likely to be useful in conjunction with the types of imaging studies that the clinic performs and for the type of patient treated by the clinic. A clinic that services a wider variety of patient types and/or performs a wider variety of imaging studies may purchase a larger and more varied set of modules. The modules may include at least one of one or more types of bases 110; two or more posts 112, 114 having associated plates 116, 118; a variety of panels 120 and 122; and a variety of panel inserts 124. One or more modules may be replaced with another module in-between imaging studies. Accordingly, imaging may be performed from a variety of perspectives without moving the patient, which is conducive to improved image registration of multiple acquired images, consistency of variables between images (associated with patient position), patient comfort and reducing time used to acquire images.

The patient support apparatus 102 may be reconfigured to operate as a conventional reclining patient support apparatus. In the conventional reclining configuration, panel 122 is pivotably mounted to panel 120, such as via a pivotable mounting mechanism, e.g., a hinge, for forming a chair. By adjusting the heights of each of posts 112 and 114 and/or adjusting the angle of incline of each of the plates 116 and 118 (relative to the reference plane) the angle of incline of each of the panels 120 and 122 (relative to the reference plane and/or relative to one another) can be adjusted to achieve desired positioning of the chair. The adjustment may be performed by operating a control device, such as control switch or pedal which controls actuation of a hydraulic device and/or motors driving a mechanism such as gear for affecting the adjustments.

The adjustments to the posts 112 and 114 may be coordinated with the adjustments to the angle of incline of the respective plates 116 and 118, for achieving the desired results. The coordination may be provided by a controller processing device or by one or more mechanical devices. The aforementioned adjustments to the patient support apparatus 102 may be made while the patient 108 is supported on the patient support apparatus 102. The chair may be raised and lowered, e.g., for loading and unloading the patient 108, such as by simultaneously lengthening or shortening posts 112 and 114 at the same rate without changing the angle of incline of plates 116 and 118.

Figure 7:
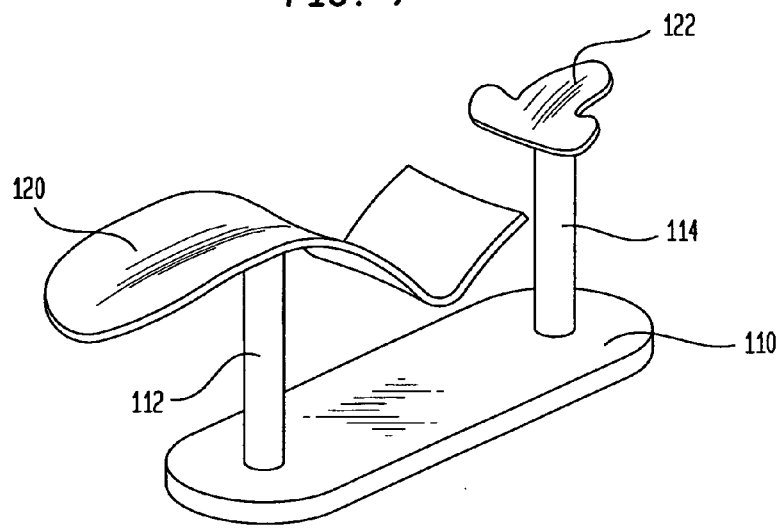
FIGS. 7-8 are perspective views of further different configurations of the patient support apparatus shown in FIG. 1.
Figure 8:
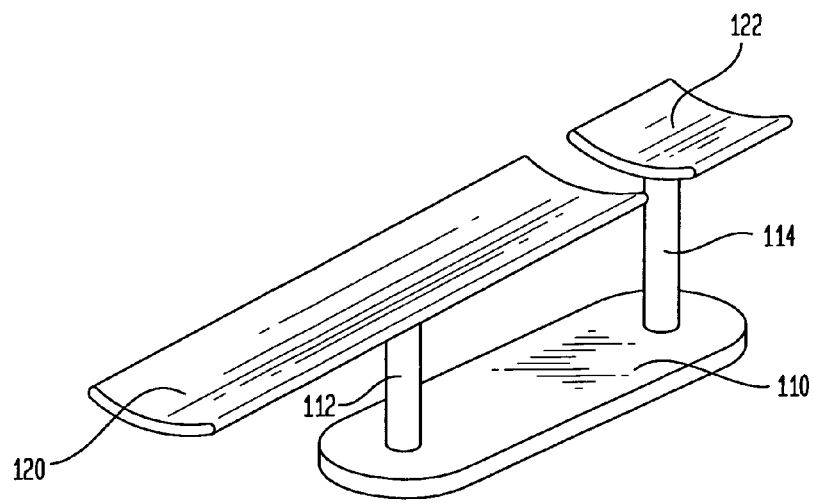

FIGS. 7 and 8 each show another configuration of the patient support apparatus 102. In FIG. 7 post 112 may be positioned under the patient's 108 thighs or pelvis, as desired, when the patient 108 is supported thereupon. The gap 140 is shown in a position that is ideal for a cardiac imaging study. In FIG. 8, the patient support apparatus 102 is shown configured as a bed having a head support and gap 140 positioned near the cardiac region of a patient 108 supported thereupon.

The patient support apparatus 102 is not limited to use with nuclear medical imaging, but may be useful with other types of imaging, such as X-ray, fluoroscopy, ultrasound, computer tomography, magnetic resonance imaging (MRI), CAT scan, positron emission tomography (PET) imaging, electrical impedance tomography, elastography, diffuse optical tomography, optoacousitic imaging, etc. Additionally, the patient support apparatus 102 is not limited to use with imaging in general, but may be useful for other medical procedure applications, where a medical procedure may be a diagnostic or therapeutic procedure. Exemplary medical procedure applications include an operating chair/table, or a chair/table for treating a patient, such as with acupuncture, acupressure, electro-muscle stimulation, massage, etc. In general, the patient support apparatus 102 is useful in a variety of applications for providing access to a patient from the top, side or underside of the patient, for reconfiguring the patient support apparatus for positioning of the patient, accommodating a variety of equipment, and/or for accommodating a variety of patient sizes.

In addition to the aforementioned advantages, the disclosed patient support apparatus 102 advantageously may be configured to accommodate each patient in accordance with his size and position assumed during treatment/imaging and in accordance with the clinical need. By accommodating the patient, the patient's comfort is improved, which will assist the patient to remain immobile during the imaging study or treatment, for providing better results, including better images.

Due to the transparency to radiation and low degree of attenuation associated with the gap 140 and or insert 124, images acquired using the disclosed nuclear medical imaging system 100 advantageously have better image quality relative to a prior art patient support apparatus. Additionally, using the disclosed nuclear medical imaging system 100, the improved image quality is achievable with the use of lower doses of radiopharmaceuticals relative to images produced using a prior art patient support apparatus. Furthermore, using the disclosed nuclear medical imaging system 100, the amount of time necessary for detecting radiation for acquiring images is decreased relative to using a prior art patient support apparatus.

Accordingly, the patient support apparatus 102 provides a high degree of versatility and features for improving the quality of image acquisition. The highly mobile patient support apparatus 102 is formed of minimal low cost materials and components. Furthermore, by mounting the medical imaging device 104 to the framework portion 106 of the patient support apparatus 102, a highly mobile and versatile patient support system 100 is provided.

It will be appreciated that various of the above-disclosed and other features and functions, or alternatives thereof, may be desirably combined into many other different systems or applications. The claims can encompass embodiments in hardware, software, or a combination thereof. Also that various presently unforeseen or unanticipated alternatives, modifications, variations or improvements therein may be subsequently made by those skilled in the art which are also intended to be encompassed by the following claims.

The invention claimed is:

1. A medical imaging system having a patient support apparatus comprising:
    a framework portion;
    a kit of rigid modular patient support panels, constructed of material having a radiation attenuation coefficient less than that of metals, the panels in selective sub-combination assembly being removably mounted to and supported by the framework portion and defining varying surface profiles, including selective gaps there between, capable of conforming a patient placed in contact with the surface profile in a range of supported body positions from supine to seated, including:
    a first set of at least one panel for supporting a patient during a first imaging study by the medical imaging system, wherein the at least one panel of the first set of at least one panel has a gap defined therein and a non-supportive panel insert supported thereby that is positioned within the gap, and further wherein the panel insert has a lower radiation attenuation coefficient than the at least one panel of the first set of at least one panel; and
    a second set of at least one panel replacing the first set of at least one panel and supporting the patient during a second imaging study by the medical imaging system.

2. The medical imaging system according to claim 1, wherein the framework portion comprises:
    at least two posts of adjustable height each having a lower end mounted to a base, and an upper end;
    the plate rotatably mounted to the upper end of each post of the at least two posts; and
    at least one removable mounting mechanism for removably mounting each panel of the at least one panel of the first set of at least one panel and the second set of at least one panel to a corresponding plate of the rotatably mounted plates.

3. The medical imaging system according to claim 1, wherein the first set of at least one panel includes a first and second panel at least partially spaced in a longitudinal direction from one another when mounted to the framework portion and defining a gap there between.

4. The medical imaging system according to claim 3, wherein the size of the gap is adjustable by at least one of adjusting the framework portion, replacing the mounted first set of at least one panel with the second set of at least one panel, and adjusting the mounting of the first set of at least one panel to the framework portion.

5. The medical imaging system according to claim 3, wherein the gap provides exposure of the patient supported by the patient support apparatus to ambient air at the location of the gap during the first imaging study.

6. The medical imaging system according to claim 3, wherein the non-supportive panel insert is supported by at least one of the first and second panels.

7. The medical imaging system according to claim 5, wherein the panel insert has a smaller transverse width, than a transverse width of the first and second panels.

8. The medical imaging system according to claim 1, wherein the gap provides exposure of the patient supported by the patient support apparatus to ambient air at the location of the gap during the first imaging study.

9. The medical imaging system according to claim 1, wherein the first set of at least one panel is provided with at least one structural feature selected from the group of structural features consisting of a foot rest, a hand rip and a headrest.

10. The medical imaging system according to claim 2, further comprising a medical imaging device having at least one detector;
    wherein the at least two posts includes a third post, the at least one panel of the first set of at least one panel includes a first portion for supporting the upper body of the patient, a second portion for selecting a first leg of the patient and a third portion for supporting a second leg of the patient, wherein the first second and third portions are supported by the first, second and third posts, respectively, and an open area is defined between the second and third portions, wherein during an imaging study a detector of the at least one detector is positioned within the open area in close juxtaposition to the patient.

11. The medical imaging system according to claim 10, wherein the at least one panel of first set of at least one panel further defines a gap that is located below the patient's pelvic region while the patient is supported by the patient support apparatus.

12. The medical imaging system according to claim 2, the framework portion further comprising a mechanism for adjusting the height of at least a portion of the at least two posts.

13. The medical imaging system according to claim 2, wherein the framework portion comprises the base and the base includes means for repositioning the at least two posts relative to one another.

14. The medical imaging system according to claim 1, wherein an attenuation coefficient of the at least one panel of the first and second sets of at least one panel is formed of a first material, and the framework portion is formed of at least a second material, wherein the attenuation coefficient of the first material is substantially lower than the average attenuation coefficient of the framework portion.

15. The imaging system according to claim 2, wherein a combined surface area of the at least two plates is substantially smaller than the combined surface area of the at least one panel of the first set of at least one panel.

16. The medical imaging system according to claim 1, wherein the medical imaging is selected from the group of medical imaging consisting of X-ray, fluoroscopy, ultrasound, computer tomography, magnetic resonance imaging (MRI), CAT scan, positron emission tomography (PET) imaging, electrical impedance tomography, elastography, diffuse optical tomography and optoacousitic imaging.

17. A patient support apparatus for supporting a patient during a medical procedure comprising:
    a framework portion;
    a kit of rigid modular patient support panels, constructed of material having a radiation attenuation coefficient less than that of metals, the panels in selective sub-combination assembly being removably mounted to and supported by the framework portion and defining varying surface profiles, including selective gaps there between, capable of conforming a patient placed in contact with the surface profile in a range of supported body positions from supine to seated, including:
        a first set of at least one panel for supporting a first patient during a first medical procedure, having a non-supportive panel insert supported by the at least one panel of the first set of at least one panel and positioned within one of the selective gaps, wherein the panel insert has a lower radiation attenuation coefficient than the at least one panel of the first set of at least one panel; and
        a second set of at least one panel replacing the first set of at least one panel and supporting a second patient during a second medical procedure.

18. The patient support apparatus according to claim 17, wherein the framework portion comprises:
    at least two posts of adjustable height each having a lower end mounted to a base, and an upper end;
    a plate rotatably mounted to the upper end of each post of the at least two posts; and
    at least one removable mounting mechanism for removably mounting each panel of the at least one panel of the first set of at least one panel and the second set of at least one panel to a corresponding plate of the rotatably mounted plates.

19. The patient support apparatus according to claim 17, wherein the first set of at least one panel includes a first and second panel at least partially spaced in a longitudinal direction from one another when mounted to the framework portion and defining one of the selective gaps there between.

20. The patient support apparatus according to claim 19, wherein the size of the gap is adjustable by at least one of adjusting the framework portion, interchanging the set of at least one panel, and adjusting the mounting of the first set of at least one panel to the framework portion.

21. A medical imaging system having a patient support apparatus comprising:
    a framework portion having a base;
    a medical imaging device mounted to the base of the framework portion;
    a kit of rigid modular patient support panels, constructed of material having a radiation attenuation coefficient less than that of metals, the panels in selective sub-combination assembly being removably mounted to and supported by the framework portion and defining varying surface profiles, including selective gaps there between, capable of conforming a patient placed in contact with the surface profile in a range of supported body positions from supine to seated, including:

a first set of at least one panel for supporting a patient during a first imaging study by the medical imaging system, having a non-supportive panel insert supported by the at least one panel of the first set of at least one panel and positioned within one of the selective gaps, wherein the panel insert has a lower radiation attenuation coefficient than the at least one panel of the first set of at least one panel; and a second set of at least one panel replacing the first set of at least one panel and supporting the patient during a second imaging study by the medical imaging system.

22. The medical imaging system according to claim 21, wherein the framework portion further comprises:

at least two posts of adjustable height each having a lower end mounted to the base, and an upper end;

a plate rotatably mounted to the upper end of each post of the at least two posts; and at least one removable mounting mechanism for removably mounting each panel of the at least one panel of the first set of at least one panel and the second set of at least one panel to a corresponding plate of the rotatably mounted plates.

23. The medical imaging system according to claim 21, wherein the first set of at least one panel includes a first and second panel at least partially spaced in a longitudinal direction from one another when mounted to the framework portion and defining one of the selective gaps there between.

24. The medical imaging system according to claim 23, wherein the size of the gap is adjustable by at least one of adjusting the framework portion, replacing the mounted first set of at least one panel with the second set of at least one panel, and adjusting the mounting of the first set of at least one panel to the framework portion.

25. The medical imaging system according to claim 21, wherein the medical imaging is selected from the group of medical imaging consisting of X-ray, fluoroscopy, ultrasound, computer tomography, magnetic resonance imaging (MRI), CAT scan, positron emission tomography (PET) imaging, electrical impedance tomography, elastography, diffuse optical tomography, optoacousitic imaging.

* * * * *